(12) United States Patent
Palushi et al.

(10) Patent No.: US 11,305,049 B2
(45) Date of Patent: Apr. 19, 2022

(54) SUCTION INSTRUMENT WITH VARYING INNER DIAMETER

(71) Applicant: Acclarent, Inc., Irvine, CA (US)

(72) Inventors: Jetmir Palushi, Irvine, CA (US); Itzhak Fang, Irvine, CA (US); Ehsan Shameli, Irvine, CA (US); Henry F. Salazar, Pico Rivera, CA (US)

(73) Assignee: Acclarent, Inc., Irvine, CA (US)

( * ) Notice: Subject to any disclaimer, the term of this patent is extended or adjusted under 35 U.S.C. 154(b) by 624 days.

(21) Appl. No.: 16/002,159

(22) Filed: Jun. 7, 2018

(65) Prior Publication Data

US 2019/0374688 A1 Dec. 12, 2019

(51) Int. Cl.
*A61M 1/00* (2006.01)

(52) U.S. Cl.
CPC ............ *A61M 1/84* (2021.05); *A61M 1/7411* (2021.05); *A61M 2206/10* (2013.01); *A61M 2210/0618* (2013.01)

(58) Field of Classification Search
CPC .................................................. A61M 1/0039
See application file for complete search history.

(56) References Cited

U.S. PATENT DOCUMENTS

| | | | |
|---|---|---|---|
| 3,958,573 A * | 5/1976 | Wiley .................. | A61C 17/04 604/267 |
| 3,963,028 A * | 6/1976 | Cooley ............... | A61M 1/0039 604/264 |
| 4,863,439 A * | 9/1989 | Sanderson .......... | A61M 1/0039 604/264 |
| 4,878,900 A * | 11/1989 | Sundt .................. | A61M 1/0039 604/119 |
| 2005/0043682 A1* | 2/2005 | Kucklick ............ | A61M 3/0279 604/164.09 |
| 2005/0273063 A1* | 12/2005 | Hoell .................. | A61M 1/0039 604/317 |
| 2006/0249161 A1* | 11/2006 | Waters ................ | A61B 5/1076 128/207.18 |
| 2007/0225636 A1* | 9/2007 | Hahn .................. | A61M 1/0047 604/35 |

(Continued)

OTHER PUBLICATIONS

International Search Report and Written Opinion dated Aug. 23, 2019 for International Application No. PCT/IB2019/054208, 17 pages.

*Primary Examiner* — Catharine L Anderson
*Assistant Examiner* — Arjuna P Chatrathi
(74) *Attorney, Agent, or Firm* — Frost Brown Todd LLC

(57) ABSTRACT

A suction instrument includes a grip portion and a cannula. The grip portion includes a suction port and defines a first lumen. The cannula extends distally from the grip portion. The cannula defines a second lumen in fluid communication with the first lumen of the grip portion. The cannula includes a proximal portion and a distal portion. The proximal portion of the cannula defines a first portion of the second lumen. The first portion of the second lumen has a first cross-sectional area. The distal portion terminates into an open distal end. The distal portion of the cannula defines a second portion of the second lumen. The second portion of the second lumen has a second cross-sectional area. The second cross-sectional area is smaller than the first cross-sectional area.

20 Claims, 4 Drawing Sheets

(56) References Cited

U.S. PATENT DOCUMENTS

2008/0177251 A1\* 7/2008 Lee ..................... A61M 1/008
                                                      604/540
2013/0090665 A1\* 4/2013 Linde ................. A61M 1/0068
                                                      606/106

\* cited by examiner

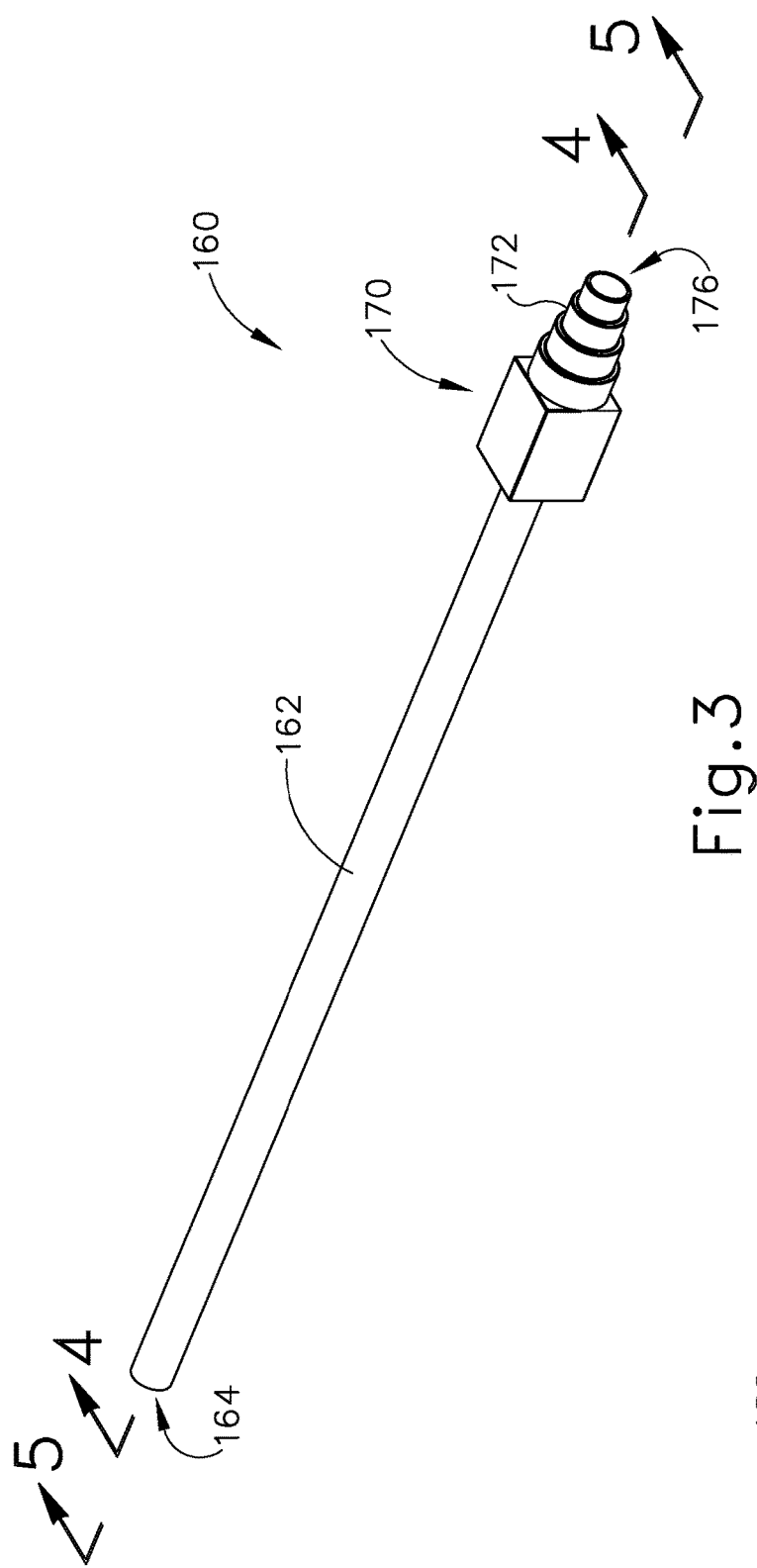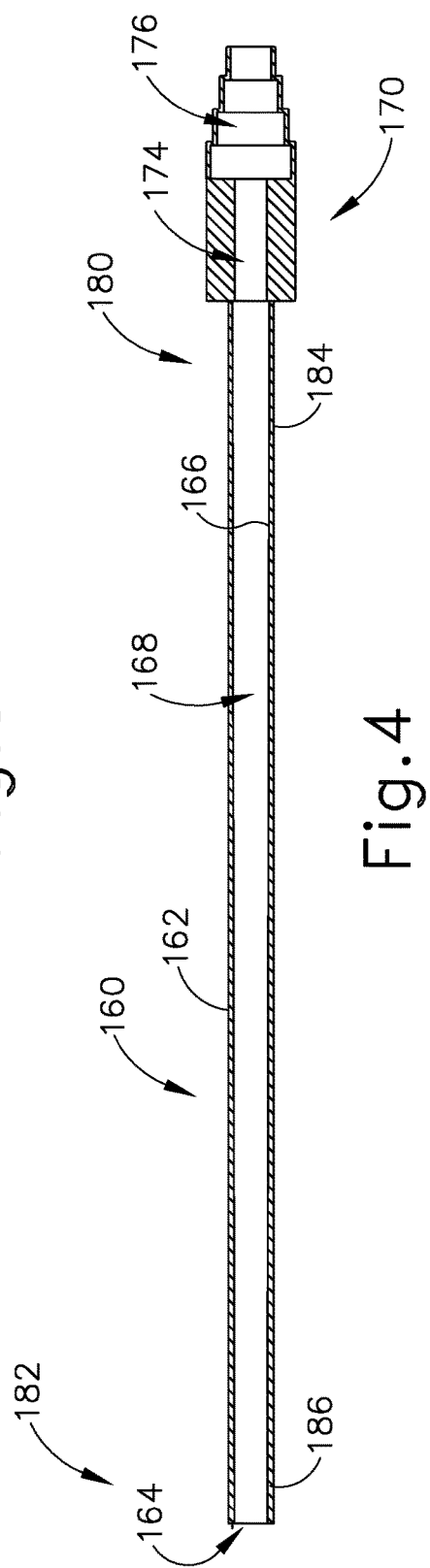
Fig.3
Fig.4

SUCTION INSTRUMENT WITH VARYING INNER DIAMETER

BACKGROUND

In some instances, it may be desirable to operate within or adjacent to an anatomical passageway of a patient, such as performing an incision of mucosa, removal of bone, or dilation of an anatomical passageway. Such operations may occur within anatomical passageways such as ostia of paranasal sinuses (e.g., to treat sinusitis), the larynx, the Eustachian tube, or other passageways within the ear, nose, or throat, etc. In addition to the above described operations, or similar operations, it may be desirable to apply suction and/or irrigation within or adjacent to an anatomical passageway before, during, or after the above described operations, or similar operations. One method of applying suction within or adjacent to an anatomical passageway of a patient involves obtaining a suction device having an elongate shaft defining a lumen terminating at an open distal end of the elongated shaft, where the lumen is in fluid communication with an external suction source. An operator may then insert the distal end of the elongate shaft within the nostril or mouth of a patient toward a desired location within the patient. With the distal end of the elongate shaft inserted within the patient, the operator may manipulate the suction device and/or suction source in order to remove extraneous and/or undesired matter near or within an anatomical passageway of a patient. Applying suction and/or irrigation during an operation may be beneficial for multiple purposes as will be apparent to those skilled in the art.

While various suction instruments have been made and used with respect to ENT surgery, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 3 depicts a perspective view of an alternative exemplary suction instrument that may be readily incorporated into the suction instrument assembly of FIG. 1;

FIG. 4 depicts a cross-sectional view of the suction instrument of FIG. 3, taken along line 4-4 of FIG. 3;

Figure 1:
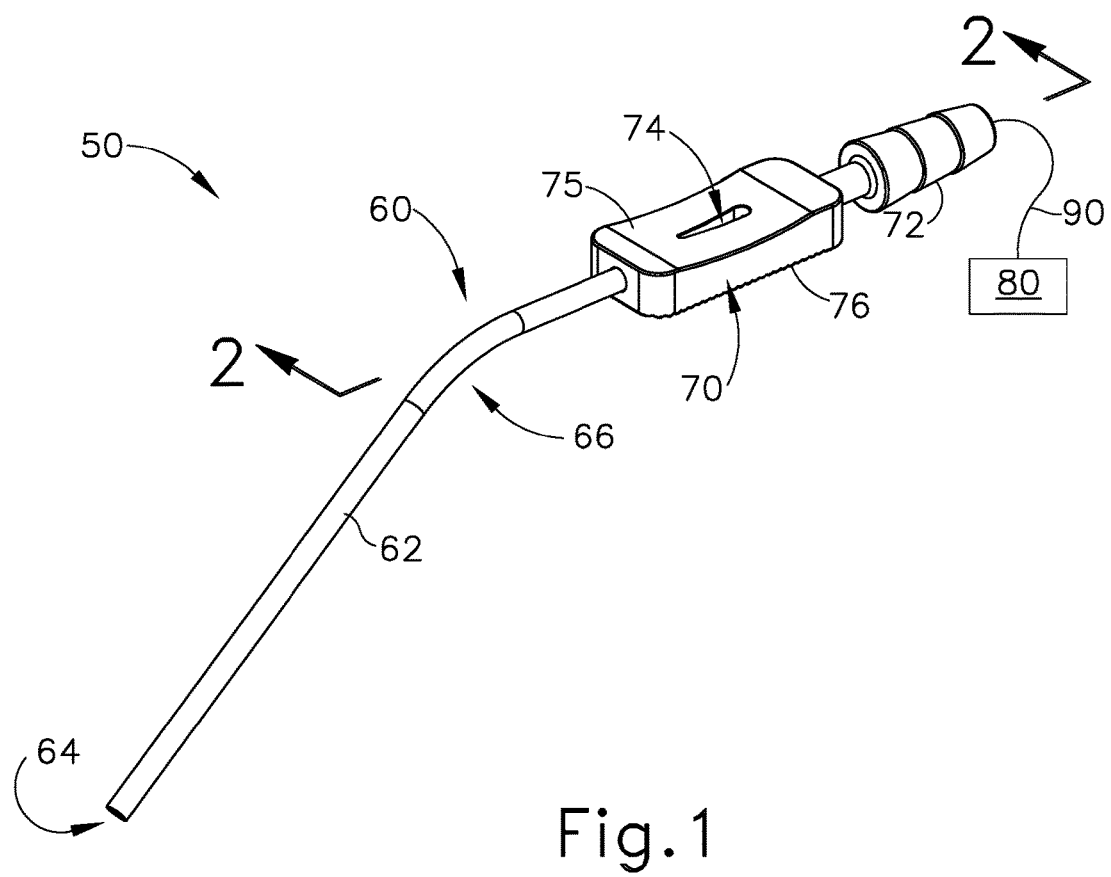
FIG. 1 depicts a perspective view of an exemplary suction instrument assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. EXEMPLARY SUCTION INSTRUMENT ASSEMBLY

Figure 2:
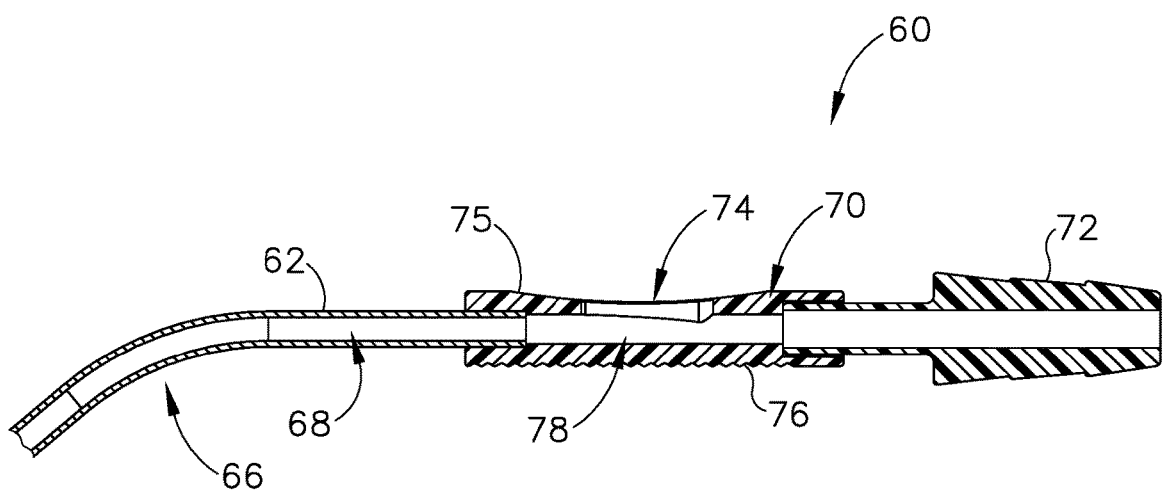
FIG. 2 depicts a cross-sectional side view of a suction instrument of the suction instrument assembly of FIG. 1, taken along line 2-2 of FIG. 1.

Various surgical procedures may warrant the use of a suction instrument in order to clear fluids and/or debris from the surgical field and/or from other sites within a patient. For instance, suction may be desirable in FESS procedures, sinuplasty procedures, and/or in various other ENT procedures. FIGS. 1-2 show an exemplary suction instrument assembly (50) that may be used to provide suction in such procedures. As shown, instrument assembly (50) includes a suction instrument (60) that is fluidly coupled with a suction source (80) via a conduit (90). Suction source (80) may comprise a vacuum pump and a fluid reservoir, among other components, as is known in the art. Suction source (80) is configured to provide enough suction to pull excess fluid and/or debris through suction instrument (60).

Suction instrument (60) of this example comprises an elongate cannula (62) extending distally from a grip portion (70). Cannula (62) has an open distal end (64) and a bent region (66) formed just distal to grip portion (70). Bent region (66) defines a bend angle that is selected to facilitate insertion of distal end (64) in a patient by an operator grasping grip portion (70). Various suitable bend angles that may be used will be apparent to those of ordinary skill in the art in view of the teachings herein.

In the present example, cannula (62) is rigid such that cannula (62) maintains the bend of bent region (66) and does not buckle during insertion into a patient's nasal cavity. By way of example only, cannula (62) may be formed of stainless steel (e.g., a stainless steel hypotube, etc.) and/or any other suitable rigid material. Also in the present example, cannula (62) defines a lumen (68) with a diameter of approximately 2.44 mm. Alternatively, any other suitable diameter may be used. It should also be understood that lumen (68) may have an elliptical cross-sectional profile or some other non-circular cross-sectional profile, if desired. A non-circular cross-sectional profile may provide additional clearance for other instruments to be positioned simultaneously in the same anatomical passageway (e.g., nasal cavity) with cannula (62).

Grip portion (70) of the present example includes a proximal suction conduit port (72) that is configured to couple with conduit (90). In the present example, port (72) has a barbed configuration to promote a secure fit with an elastomeric conduit (90), though it should be understood that various other kinds of configurations may be used for port (72). Grip portion (70) of the present example further includes a transverse vent opening (74) formed through an upper surface (75); and a lower surface (76). As best seen in FIG. 4, vent opening (74) is in fluid communication with a lumen (78) formed through grip portion (70). Vent opening (74) has a teardrop shape in the present example, though it should be understood that vent opening (74) may have any other suitable shape. By way of example only, the teardrop shape (or some other elongate shape) may enable the operator to selectively vary the amount of suction based on the longitudinal position of the operator's thumb (or other finger) on vent opening (74). Lumen (78) is further in fluid communication with port (72) and a lumen (68) of cannula (62). It should be understood that lumens (68, 78) cooperate to provide an unobstructed fluid path from port (72) to open distal end (64) of cannula (62).

Surfaces (75, 76) are configured to promote gripping of grip portion (70) by an operator. In particular, upper surface (75) provides a concave contour while lower surface (76) provides a series of ridges. By way of example only, an operator may grasp grip portion (70) by placing a thumb on upper surface (75) and the side of the index finger of the same hand on lower surface (76). The rectangular shape of grip portion (70) may provide the operator with substantial purchase on grip portion (70), while the configurations of surfaces (75, 76) may further secure the operator's grip.

During use of suction instrument assembly (50), the operator may grasp grip portion (70) and position distal end (64) of cannula (62) at a target site in a patient. In some such instances, suction source (80) remains in a constantly activated state. In those instances, the operator may leave vent opening (74) uncovered as the operator positions instrument (60) relative to the patient. This may result in suction source (80) drawing suction through vent opening (74) without drawing suction through open distal end (64). When the operator wishes to apply the suction to the target site in the patient via open distal end (64), the operator may simply cover vent opening (74) with the operator's thumb (or otherwise cover vent opening (74)). The operator may thus selectively cover and uncover vent opening (74) during a procedure in order to selectively apply suction.

While the above and below examples are provided in the context of suction instruments, it should be understood that the same instruments (and variations thereof) may be used to provide fluid irrigation at a target site in a patient; or to provide various other kinds of functionality. The teachings herein are thus not limited to suction instruments and operations per se. Other suitable instruments and procedures in which the teachings herein may be applied will be apparent to those of ordinary skill in the art.

II. EXEMPLARY SUCTION INSTRUMENT WITH VARYING INNER DIAMETER

In some instances, during use of suction instrument assembly (50), tissue particles and/or other debris may become jammed, clogged, or otherwise obstructed within a portion of the suction line (i.e. from open distal end (64), through lumens (68, 78), conduit (90), and into suction source (80)). If such an obstruction occurs within the suction line, fluid communication between open distal end (64) and suction source (80) may become blocked such that open distal end (64) may no longer apply a suitable amount of suction to the desired target site. In such instances, the operator may have to remove elongated cannula from the patient, clear the obstruction such that suction source (80) may communicate a suitable amount of suction force to open distal end (64), and then re-insert elongate cannula (62) in the desired nasal cavity of the patient. This may undesirably add time to the duration of the medical procedure.

In some instances, elongate cannula (62) may be substantially long or have a bent region (66), such that if an obstruction occurs within lumen (68) of cannula (62), it may occur within a portion of lumen (68) that is difficult to access for purposes of unclogging obstructing tissue and/or debris. This may further add time and inconvenience to a medical procedure.

In view of the foregoing, it may be desirable for suction instrument (60) to define lumen (68) with a varying cross-sectional area along the length of elongate cannula (62). The portion of cannula (62) defining lumen (68) with the smallest cross-sectional area may be the location where, if an obstruction does occur, the obstruction may be located at that specific location along lumen (68). Additionally, the portion of cannula (62) defining lumen (68) with the smallest cross-sectional area may be located at a specific location that is relatively easy to access compared to other portions of lumen (68).

Figure 5:
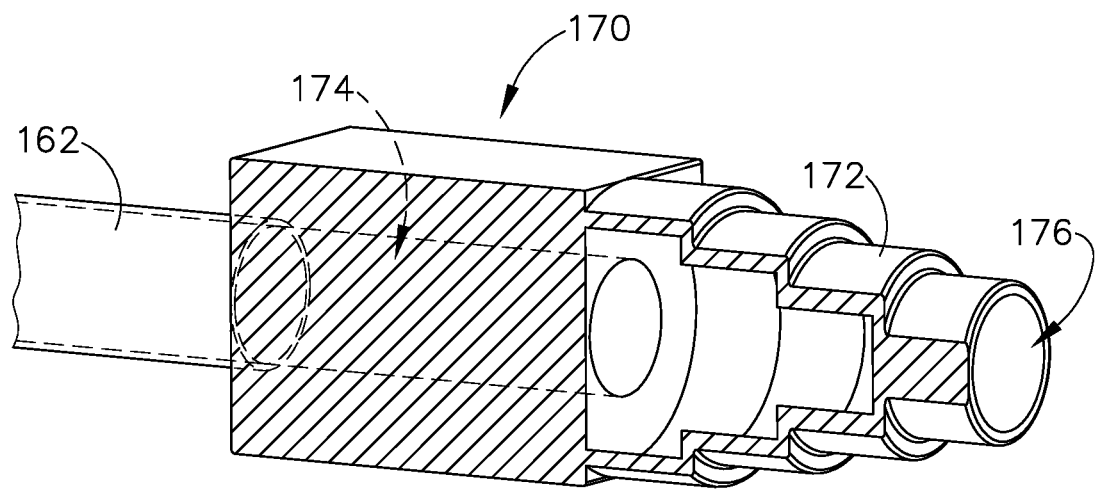
FIG. 5 depicts a cross-sectional view of a grip portion of the suction instrument of FIG. 3.

FIGS. 3-5 show an exemplary suction instrument (160) that may be readily incorporated into suction instrument assembly (50) in replacement of suction instrument (60) described above. Suction instrument (160) may be substantially similar to suction instrument (60) described above, with differences elaborated below. Therefore, suction instrument (160) may fluidly couple with suction source (80) via conduit (90). Suction instrument (160) includes an elongate cannula (162) extending distally from a grip portion (170). As will be described in greater detail below, elongate cannula (162) defines a lumen (168) having a varying cross-sectional area along the length of cannula (162). The varying cross-section area is dimensioned such that if an obstruction occurs, the obstruction is controlled toward a distal portion (182) of elongate cannula (162).

Grip portion (170) includes a proximal suction conduit port (172) that is configured to couple with conduit (90). In the present example port (172) has a barbed configuration to promote a secure fit with an elastomeric conduit (90), though various other kinds of configurations may be used for port (170). As best seen in FIG. 5, grip portion (170) defines a lumen (174) while port (172) also defines a step-down lumen (176) having various, progressively smaller diameters in the current example. While in the current example, port (172) defines a step-down lumen, any other suitably type of lumen may be used as would be apparent to one having ordinary skill in the art in view of the teachings herein. Lumens (174, 176) are in fluid communication with each other such that when elastomeric conduit (90) is coupled with port (172), conduit (90) is in fluid communication with both lumens (174, 176). While not shown, grip portion (170) may have various structural features of grip portion (70) described above. For instance, grip portion (170) may have a transverse vent opening like a transverse vent opening (74) of grip portion (70).

Cannula (162) extends between a proximal portion (180) and a distal portion (182) and terminates distally into an open distal end (164). In the present example, cannula (162) is dimensioned for insertion into a patient's nasal cavity. While in the current example, elongate cannula (162) extends from proximal portion (180) to distal portion (182) in a substantially straight manner without having a bent region, this is merely optional. Elongate cannula (162) may have any suitable bent region, for promoting access into various nasal cavities, the Eustachian tube, etc., as would be apparent to one having ordinary skill in the art in view of the teachings herein. In the present example, cannula (162) is rigid such that cannula (162) does not buckle during insertion into a patient's nasal cavity. Additionally, cannula (162) is rigid such that if cannula (162) had a bent region, the bend of bent region is maintained during insertion into the patient's nasal cavity. By way of example only, cannula (162) may be formed of stainless steel (e.g., a stainless steel hypotube, etc.) and/or any other suitable rigid material.

Cannula (162) defines a lumen (168) that extends from open distal end (164) all the way into grip portion (170) such that lumen (168) of cannula (162) is in fluid communication with lumens (174, 176) of grip portion. Therefore, when properly assembled with conduit (90) and suction source (80), lumen (168) is in fluid communication with suction source (80) such that open distal end (164) may apply suction during exemplary use.

As best seen in FIG. 4, cannula (162) includes a tapered interior surface (166) that defines lumen (168). Tapered interior surface (166) extends distally at an angle such the cross-sectional area of lumen (168) located at distal portion (182) of cannula (162) is smaller than the cross-sectional area of lumen (168) located at proximal portion (180) of cannula (162). In particular, tapered interior surface (166) is angled such that the cross-sectional area of lumen (168) at open distal end (164) has the smallest cross-sectional area. Therefore, during exemplary use, if an obstruction within lumen (168) were to occur, the obstruction is most likely to occur at open distal end (164) such that the operator may remove elongate cannula (162) from the patient and easily clear the obstruction by accessing open distal end (164) to remove excess tissue and/or debris. While open distal end (164) has the smallest cross-sectional area of lumen (168), open distal end (164) may also have the smallest cross-sectional area as compared to lumens (174, 176) and conduit (90) as well.

In some instances, the tapered configuration of lumen (168) may also provide a more turbulent flow of fluid as the fluid is suctioned proximally through lumen (168). This turbulence may further prevent the occurrence of debris forming clogs or other obstructions in lumen (168). In other words, the turbulently flowing fluid may agitate the debris to thereby prevent the debris from substantially adhering to the sidewall of lumen (168).

In the present example, lumen (168) is circular in nature, such that the cross-sectional area of lumen (168) along the length of cannula (162) is defined by the corresponding inner diameter of tapered interior surface (166). However, this is merely illustrative. Tapered interior surface (166) defining lumen (168) may instead be configured to provide lumen (168) with an oval shaped cross-sectional profile, a triangle shaped cross-sectional profile, a square shaped cross-sectional profile, or any other suitable shaped cross-sectional profile as would be apparent to one having ordinary skill in the art in view of the teachings herein. Additionally, different portions of lumen (168) may have different cross-sectional shapes. For example, proximal portion (180) of cannula (162) may have lumen (168) defined in a square cross-sectional shape while distal portion (182) of cannula (162) may have lumen (168) defined in a circular cross-sectional shape.

In the present example, tapered interior surface (166) extends distally such that proximal portion (180) has a first thickness (184) and distal portion (182) has a second thickness (186) smaller than first thickness (184). However, this is merely optional. For example, first thickness (184) and second thickness (186) may be equal to each other, such that the outer diameter of cannula (162) tapers in parallel with the taper of the inner diameter defining lumen (168).

In the present example, tapered interior surface (166) has a single, consistent taper angle such that the cross-sectional area of lumen (168) deviates in a uniform fashion. However, tapered interior surface (166) may be deviate in cross-sectional area in any other suitable manner as would be apparent to one having ordinary skill in the art in view of the teachings herein. For example, tapered interior surface (166) may extend distally at various angles such that the cross-sectional area of lumen (168) decreases non-uniformly as cannula (162) extends distally. As another merely illustrative example, tapered interior surface (166) may extend distally in an undulating fashion. In fact, as will be described in greater detail below, having tapered interior surface (166) is entirely optional.

Figure 6:
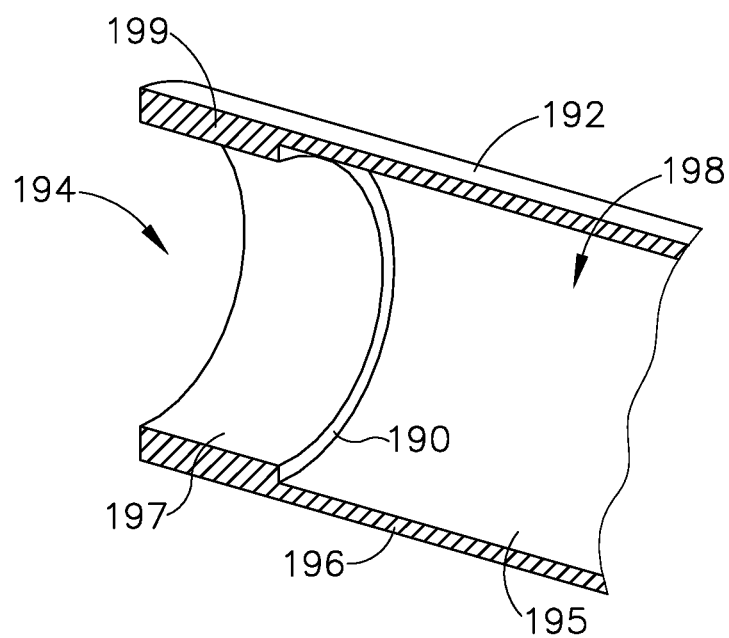
FIG. 6 depicts a cross-sectional view of a distal end of an alternative exemplary cannula that may be readily incorporated into the suction instrument of FIG. 3.

FIG. 6 shows a distal end of an alternative elongate cannula (192) that may be readily incorporated into suction instrument (160). Similar to cannula (162) described above, elongate cannula (192) may extend from grip portion (170) and terminate distally into an open distal end (194). In the present example, cannula (192) is dimensioned for insertion into a patient's nasal cavity. While in the current example, elongate cannula (192) extends in a substantially straight manner without having a bent region, this is merely optional. Elongate cannula (192) may have any suitable bent region, for promoting access into various anatomical regions associated with a patient's nasal cavity or throat, etc., as would be apparent to one having ordinary skill in the art in view of the teachings herein. In the present example, cannula (192) is rigid such that cannula (192) does not buckle during insertion into a patient's nasal cavity. Additionally, cannula (192) is rigid such that if cannula (192) had a bent region, the bend of the bent region would be maintained during insertion into the patient's nasal cavity. By way of example only, cannula (192) may be formed of stainless steel (e.g., a stainless steel hypotube, etc.) and/or any other suitable rigid material.

Cannula (192) defines a lumen (198) that extends from open distal end (194) all the way into grip portion (170) such that lumen (198) of cannula (192) is in fluid communication with lumens (174, 176) of grip portion. Therefore, when properly assembled with conduit (90) and suction source (80), lumen (198) is in fluid communication with suction source (80) such that open distal end (194) may apply suction during exemplary use.

However, instead of having a tapered interior surface (166), cannula (192) of the present example includes a proximal, first, interior surface (195) and a distal, second, interior surface (197). The portion of cannula (192) having proximal interior surface (195) comprises a first thickness (196); while the portion of cannula (192) having distal interior surface (197) comprises a second thickness (199). Second thickness (199) is greater than first thickness (196).

Proximal interior surface (196) and distal interior surface (197) together define lumen (198) and are connected to each other by a proximally facing step surface (190). Distal interior surface (197) defines a portion of lumen (198) having a smaller cross-sectional area as compared to the portion of lumen (198) defined by proximal interior surface (195). Therefore, during exemplary use, if an obstruction within lumen (198) were to occur, the obstruction is most likely to occur at open distal end (194) such that the operator may remove elongate cannula (192) from the patient and easily clear the obstruction by accessing open distal end (194) to remove excess tissue and/or debris. While open distal end (194) has the smallest cross-sectional area of lumen (198), open distal end (194) may also have the smallest cross-sectional area as compared to lumens (174, 176) and conduit (90) as well.

In the current example, step surface (190) extends substantially radially between interior surfaces (195, 197); however, this is merely optional. For instance, step surface (190) may extend between interior surface (195, 197) at a slanted angle between interior surfaces (195, 197). In other words, the transition between interior surfaces (195, 197) need not necessarily be stepped. The transition may instead be tapered, curved, or otherwise configured.

In the present example, lumen (198) is circular in nature, such that the cross-sectional area of lumen (198) along the length of cannula (192) is defined by the corresponding diameter of proximal interior surface (195) and distal interior surface (197). However, this is merely illustrative. Interior surfaces (195, 197) defining lumen (198) may instead be configured to provide lumen (198) with an oval shaped cross-sectional profile, a triangle shaped cross-sectional profile, a square shaped cross-sectional profile, or any other suitable shaped cross-sectional profile as would be apparent to one having ordinary skill in the art in view of the teachings herein. Additionally, proximal interior surfaced (195) and distal interior surface (197) defining lumen (198) may have different cross-sectional shapes. For example, proximal interior surface (195) of cannula (192) may have lumen (198) defined in a square cross-sectional shape while distal interior surface (197) of cannula (192) may have lumen (198) defined in a circular cross-sectional shape.

Figure 7:
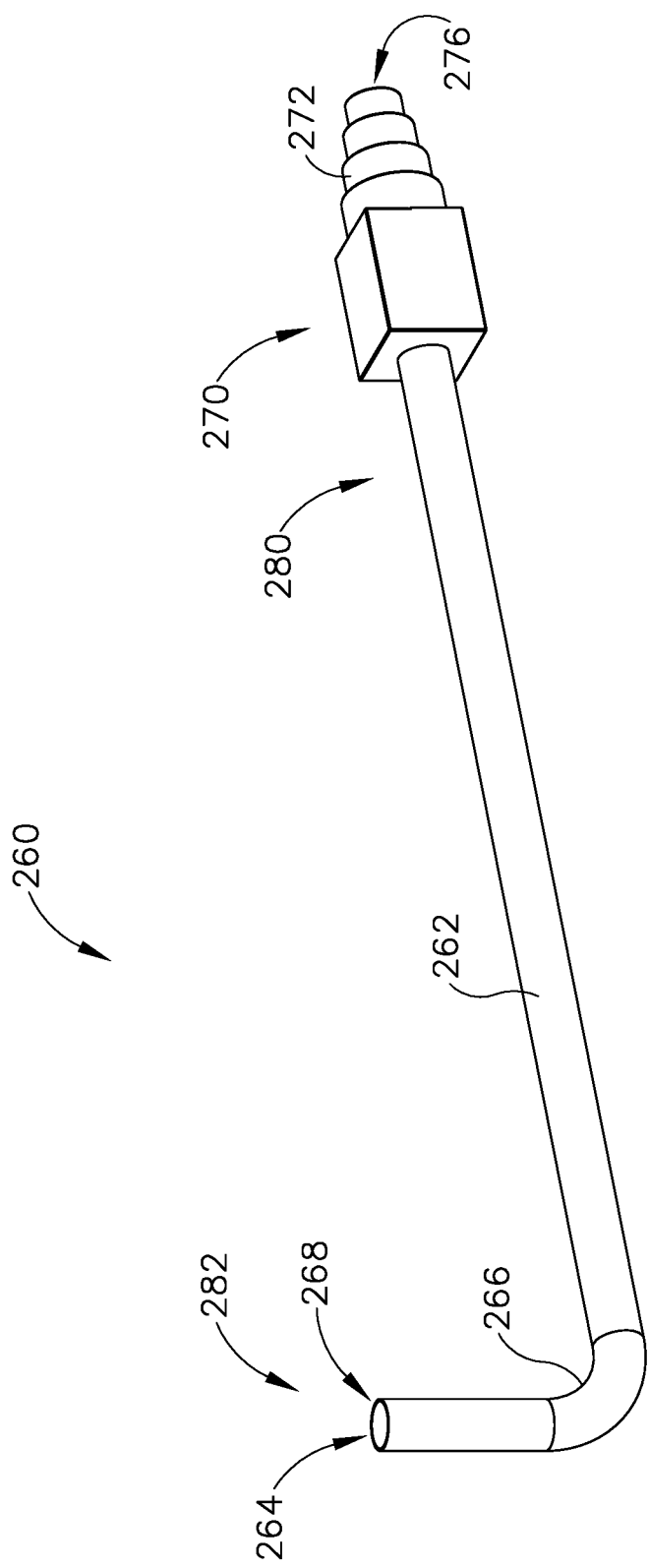
FIG. 7 depicts a perspective view of an alternative exemplary suction instrument that may be readily incorporated into the suction instrument assembly of FIG. 1.

As mentioned above, cannulas (162, 192) may be configured to have a bent region. FIG. 7 shows an exemplary suction instrument (260) having a bent region (266). Suction instrument (260) of this example is substantially similar to suction instrument (160) described above, except that instrument (260) has cannula (262) with a bent region (266) rather than being substantially straight. Suction instrument (260) includes cannula (262) and grip portion (270). Grip portion (270) is substantially similar to grip portion (170) described above. Grip portion (270) of this example thus includes a proximal suction conduit (272) defining a step-down lumen (276) substantially similar to proximal suction conduit (172) and step-down lumen (176) described above, respectively. While not shown, grip portion (270) may have various structural features of grip portion (70) described above. For instance, grip portion (270) may have a transverse vent opening like a transverse vent opening (74) of grip portion (70).

Elongate cannula (262) is substantially similar to elongate cannula (162) described above, with differences elaborated below. Elongate cannula (262) extends from a proximal portion (280) connected to grip portion (270) all the way to distal portion (282) terminating at an open distal end (264). As mentioned above, elongate cannula (262) includes a bent region (266). In the current example, bent region (266) defines a bend angle of approximately 90 degrees. However, any suitable bend angle may be used as would be apparent to one having ordinary skill in the art.

Elongate cannula (262) defines a lumen (268) that may be substantially similar to either lumen (168, 198) described above. In some versions, lumen (268) has a cross-sectional area at the distal portion (282) (e.g., at open distal end (264)), of cannula (262) that is smaller than the cross-sectional area of lumen (268) along the rest of the length of cannula (262). Therefore, during exemplary use, if an obstruction within lumen (268) were to occur, the obstruction is most likely to occur at open distal end (294) such that the operator may remove elongate cannula (262) from the patient and easily clear the obstruction by accessing open distal end (264) to remove excess tissue and/or debris.

In some other versions, lumen (268) has a cross-sectional diameter that is constant along the entire length of lumen (268). This would include the portion of lumen (268) along bent region (266). In other words, the diameter of lumen (268) is in no way reduced along any portion of bent region (266) in some versions. This may prevent the occurrence of debris forming clogs or other restrictions along bent region (266), which may otherwise occur in versions where the diameter of lumen (268) is in any way reduced along a portion of bent region (266).

In some versions of the process of forming suction instrument (260), cannula (262) may start out as a linear piece that is subsequently bent to form bent region (266). In some such instances, the region where the bend occurs may have a significant reduction is cross-sectional area. In such instances, open distal end (264) may be dimensioned such that the cross-sectional area of lumen (268) at open distal end (264) is still smaller than the cross-sectional area of lumen (268) at recently formed bent region (266). By having the diameter of lumen (268) at the region distal to bent region (266) be smaller than the diameter of lumen (268) along bent region (266), this may reduce the occurrence of debris forming clogs or other restrictions along bent region (266).

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A suction instrument, comprising: (a) a grip portion comprising a suction port, wherein the grip portion defines a first lumen; and (b) a cannula extending distally from the grip portion, wherein the cannula defines a second lumen in fluid communication with the first lumen of the grip portion, wherein the cannula comprises: (i) a proximal portion connected to the grip portion, wherein the proximal portion of the cannula defines a first portion of the second lumen, wherein the first portion of the second lumen has a first cross-sectional area, and (ii) a distal portion terminating into an open distal end, wherein the distal portion of the cannula defines a second portion of the second lumen, wherein the second portion of the second lumen has a second cross-sectional area, wherein the second cross-sectional area is smaller than the first cross-sectional area.

Example 2

The suction instrument of Example 1, wherein the second cross-sectional area is located at the open distal end of the cannula.

Example 3

The suction instrument of any one or more of Examples 1 through 2, wherein the cannular further comprises a tapered interior surface.

Example 4

The suction instrument of Example 3, wherein the tapered interior surface extends between the first cross-sectional area and the second cross-sectional area.

Example 5

The suction instrument of Example 4, wherein the tapered interior surface defines the second lumen.

Example 6

The suction instrument of any one or more of Examples 1 through 5, wherein the first cross-sectional area forms a circle.

Example 7

The suction instrument of any one or more of Examples 1 through 6, wherein the second cross-sectional area forms a circle.

Example 8

The suction instrument of any one or more of Examples 1 through 7, wherein the proximal portion of the cannula has a first thickness.

Example 9

The suction instrument of Example 8, wherein the distal portion of the cannula has a second thickness.

Example 10

The suction instrument of Example 9, wherein the first thickness is greater than the second thickness.

Example 11

The suction instrument of Example 9, wherein the second thickness is greater than the first thickness.

Example 12

The suction instrument of any one or more of Examples 1 through 11, wherein the cannula includes a bent region located between the proximal portion and the distal portion.

Example 13

The suction instrument of Example 12, wherein the bent region forms a 90-degree angle between the proximal portion and the distal portion.

Example 14

The suction instrument of any one or more of Examples 1 through 13, wherein the suction port comprises a barbed feature.

Example 15

The suction instrument of any one or more of Examples 1 through 14, wherein the first lumen comprises a third cross-sectional area.

Example 16

The suction instrument of Example 15, wherein the third cross-sectional area is larger than the second cross-sectional area.

Example 17

A suction instrument, comprising a cannula dimensioned for insertion into a nasal cavity of a patient, wherein the cannula defines a lumen, wherein the cannula comprises: (a) a proximal portion, wherein the proximal portion of the cannula defines a first portion of the lumen, wherein the first portion of the lumen has a first diameter, and (b) a distal portion and terminating into an open distal end, wherein the distal portion of the cannula defines a second portion of the lumen, wherein the second portion of the lumen has a second diameter, wherein the second diameter is smaller than the first diameter area.

Example 18

The suction instrument of Example 17, wherein the cannula further comprises a tapered interior surface extending between the proximal portion and the distal portion.

Example 19

The suction instrument of Example 18, wherein the tapered interior surface extends along a constant angle.

Example 20

A suction instrument, comprising a cannula dimensioned for insertion into the nasal cavity of a patient, wherein the cannula defines a lumen, wherein the cannula comprises: (a) a proximal portion, wherein the lumen associated with the proximal portion has a first diameter; (b) a distal portion and terminating into an open distal end, wherein the lumen associated with the distal portion has the first diameter; and (c) a bent portion located between the proximal portion and the distal portion, wherein the lumen associated with the bent portion also has the first diameter such that the first diameter is maintained along the entire length of the lumen extending from the proximal portion to the distal portion and along the bent portion.

IV. MISCELLANEOUS

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. In some instances, the instrument may be placed in a reprocessing tray (e.g., a metal bin or basket) and then cleaned in a surgical instrument washer. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, steam, hydrogen peroxide vapor (e.g., via a STERRAD sterilization system by Advanced Sterilization Products of Irvine, Calif.), and/or using any other suitable systems or techniques.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A suction instrument, comprising:
   (a) a grip portion comprising a suction port and a plurality of distally facing step-down surfaces, wherein the grip portion defines a first lumen and a proximal step-down lumen terminating into a proximal end, wherein the proximal step-down lumen is in communication with the first lumen, wherein the first lumen has a first diameter, wherein the proximal step-down lumen has an array of diameters that decrease in size toward the proximal end due to the plurality of distally facing step-down surfaces, wherein at least one diameter in the array of diameters is smaller than the first diameter; and
   (b) a cannula extending distally from the grip portion, wherein the cannula defines a second lumen in fluid communication with the first lumen of the grip portion, wherein the cannula comprises:
      (i) a proximal portion connected to the grip portion, wherein the proximal portion of the cannula defines a first portion of the second lumen, wherein the first portion of the second lumen has a first cross-sectional area, and
      (ii) a distal portion terminating into an open distal end, wherein the distal portion of the cannula defines a second portion of the second lumen, wherein the second portion of the second lumen has a second cross-sectional area, wherein the second cross-sectional area is smaller than the first cross-sectional area.

2. The suction instrument of claim 1, wherein the second cross-sectional area is located at the open distal end of the cannula.

3. The suction instrument of claim 1, wherein the cannula further comprises a tapered interior surface.

4. The suction instrument of claim 3, wherein the tapered interior surface extends between the first cross-sectional area and the second cross-sectional area.

5. The suction instrument of claim 4, wherein the tapered interior surface defines the second lumen.

6. The suction instrument of claim 1, wherein the first cross-sectional area forms a circle.

7. The suction instrument of claim 6, wherein the second cross-sectional area forms a circle.

8. The suction instrument of claim 1, wherein the proximal portion of the cannula has a first thickness.

9. The suction instrument of claim 8, wherein the distal portion of the cannula has a second thickness.

10. The suction instrument of claim 9, wherein the first thickness is greater than the second thickness.

11. The suction instrument of claim 9, wherein the second thickness is greater than the first thickness.

12. The suction instrument of claim 1, wherein the cannula includes a bent region located between the proximal portion and the distal portion.

13. The suction instrument of claim 12, wherein the bent region forms a 90-degree angle between the proximal portion and the distal portion.

14. The suction instrument of claim 1, wherein the suction port comprises a barbed feature.

15. The suction instrument of claim 1, wherein the first lumen comprises a third cross-sectional area.

16. The suction instrument of claim 15, wherein the third cross-sectional area is larger than the second cross-sectional area.

17. A suction instrument, comprising a cannula dimensioned for insertion into a nasal cavity of a patient, wherein the cannula defines a lumen, wherein the cannula comprises:
    (a) a proximal portion, wherein the proximal portion of the cannula defines a first portion of the lumen, wherein the first portion of the lumen has a first diameter; and
    (b) a distal portion extending along an axis and terminating into an open distal end, wherein the distal portion of the cannula defines a second portion of the lumen located at the open distal end and a third portion of the lumen extending proximally from the second portion, wherein the distal portion comprises a radial step surface connecting the second portion with the third portion, wherein the radial step surface extends along a plane that is perpendicular relative to the axis of the distal portion, wherein the second portion of the lumen has a second diameter, wherein the third portion of the lumen has a third diameter, wherein the second diameter is smaller than both the first diameter and the third diameter.

18. The suction instrument of claim 17, wherein the cannula further comprises a tapered interior surface extending between the proximal portion and the distal portion.

19. The suction instrument of claim 18, wherein the tapered interior surface extends along a constant angle.

20. A suction instrument, comprising a cannula dimensioned for insertion into a nasal cavity of a patient, wherein the cannula defines a lumen, wherein the cannula comprises:
    (a) a proximal portion, wherein the lumen associated with the proximal portion has a first diameter;
    (b) a distal portion extending along a long axis and terminating into an open distal end, wherein the lumen associated with the distal portion comprises a second diameter associated with the open distal end, a radial step-down surface located proximal relative to the second diameter and extending along a plane that is perpendicular with the long axis of the distal portion, and a third diameter located proximal relative to the radial-step down surface, wherein the second diameter is smaller than both the first diameter and the third diameter; and
    (c) a bent portion located between the proximal portion and the distal portion.

* * * * *